United States Patent
Green et al.

(12) 
(10) Patent No.: US 6,300,547 B1
(45) Date of Patent: *Oct. 9, 2001

(54) MANDELVILLA PLANT WITH DOUBLE FLOWER

(75) Inventors: James Mitchell Green; Cecil Michael Green, Jr.; Rita Marie Green, all of Haines City, FL (US)

(73) Assignee: Monrovia Nursery Company, Azusa, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/137,561

(22) Filed: Aug. 20, 1998

(51) Int. Cl.[7] ............................... A01H 5/00; A01H 5/02; A01H 5/04; A01H 5/12; A01H 4/00

(52) U.S. Cl. ............................. 800/323; 800/298; 800/260

(58) Field of Search ................................. 800/298, 323, 800/232, 260, 270; Plt./232; 47/DIG. 3, 58.1

(56) References Cited

U.S. PATENT DOCUMENTS 5,744,693 * 4/1998 Meyerowitz et al. ............... 800/205

OTHER PUBLICATIONS

Huxley [Ed.] The New Royal Horticultual Society Dictionary of Gardening. The Macmillian Press Limited, London. p. 187, 1992.*
Weigel et al. The ABCs of Floral Homotic Genes. Cell. vol. 78, pp. 203–209, 1994.*
Color photographer of MandeVilla plant 'Monite' (1 page).
Letter bearing a date of Aug. 22, 1996 from Mike C. Green (11 pages).
Memo entitled MN–AZUSA dated Sep. 4, 1996 (3 pages).
J. Mitchell Green letter bearing the notation Jun. 21, 1997 (wrote) mailed Jul. 1, 1997 (8 pages).
Letter from Monrovia to Mitchell Green bearing facsimile notation of Aug. 21, 1997 (1 page).

* cited by examiner

*Primary Examiner*—Paula Hutzell
*Assistant Examiner*—Melissa Kimball
(74) *Attorney, Agent, or Firm*—Klarquist Sparkman Campbell Leigh & Whinston LLP

(57) ABSTRACT

A new "Double Mandevilla" variety is characterized by double flowers which present an outer corolla and a ring of inner petaloids producing an enhanced decorative appearance for this evergreen vine-like climbing shrub.

10 Claims, 3 Drawing Sheets

(3 of 3 Drawing Sheet(s) Filed in Color)

MANDELVILLA PLANT WITH DOUBLE FLOWER

FIELD OF THE INVENTION

The present invention relates to a new variety of Mandevilla plant with a double flower.

BACKGROUND OF THE INVENTION

Mandevillas are woody, evergreen, vine-like climbing shrubs with funnel-shaped or trumpet-shaped flowers that grow in temperate climates. Common varieties of Mandevilla include *Mandevilla X amabilis* ('Alice du Pont') which exhibits red to red-purple, trumpet-like flowers; *Mandevilla sanderi* ('Red Riding Hood') which exhibits rose-pink, funnel-shaped blooms; *Mandevilla X amabilis* Summer Snow™ ('Monte'), U.S. Pat. No. 10,329, which exhibits pure white flowers which may become tinged with a pinkish blush; and *Mandevilla suaveolens* (*Mandevilla laxa*) which exhibits white to ivory trumpet shaped flowers. Mandevilla is native from Mexico to Argentina, and over 100 separate species of Mandevilla have been classified.

A Mandevilla generally has the following characteristics. Leaves are opposite or verticillate. Flowers are funnel-form, displayed in axillary or terminal racemes, the calyx is five-parted with scales at the base inside, the corolla is five-parted, the stamens have very short filaments and anthers and unite and adhere to the stigma, there is a dish of two to five lobes or scales and there are two ovaries with many ovules in each. The fruit consists of two terete follicles with the seeds having a tuft of hairs at the apex.

Mandevillas are popular garden and greenhouse plants, growing well in full sun and partial shade in temperate areas, providing year-round foliage and decorative blooms.

The presently known Mandevillas possess single funnel shaped flowers and it is believed that none of the presently known species or varieties possess double flowers, except the new variety 'Monite'.

It would be commercially desirable to produce a Mandevilla that has double flowers and which, therefore, have enhanced decorative qualities compared to currently available Mandevilla plants.

SUMMARY OF THE INVENTION

The present invention is a Mandevilla plant (referred to hereafter as "Double Mandevilla") that is different from previous Mandevilla plants in that it possesses double flowers. Particularly, Double Mandevilla plants possess both an outer corolla of petals and a generally concentric inner ring of petaloids (converted stamens). Due to the conversion of stamens to petaloids, it is likely that reproductive structures will be sterile. Double Mandevilla plants are useful as woody vines that produce decorative double blossoms. The double flowers of Double Mandevilla plants enhance appearance and make the plants especially marketable, and therefore, useful.

The present invention encompasses whole plant specimens and parts of Double Mandevilla plants including seeds, pollen, cut flowers, blooms, meristem tissue, cultured cells, rootstock, tissue that is propagatable by sexual or asexual methods, and also grafted shrubs that include Double Mandevilla rootstock or shrub or stems or parts thereof and plants that are "essentially derived" from Double Mandevilla plants.

The present invention also includes methods of producing double-flowering Mandevilla plants by sexual propagation of any non-sterile Double Mandevilla plants, whether by self-crossing Double Mandevilla or by crossing Double Mandevilla with another Mandevilla plant or other plant. The present invention also includes Mandevilla plants that are produced by such methods.

The present invention also includes methods of producing Double Mandevilla plants by asexual methods such as by cutting and somatic cell culture.

The present invention also includes the new and distinct specific variety of Double Mandevilla plant called 'Rita Marie Green'. The present invention includes whole plants of Rita Marie Green as well as parts of this variety including any seeds, any pollen, cut flowers, blooms, meristem tissue, cultured cells, rootstock, and any tissue propagatable by sexual or asexual methods, and grafted shrubs that include Rita Marie Green rootstock or shrubs or stems or parts thereof that are "essentially derived" from Rita Marie Green.

The present invention also includes methods of producing Rita Marie Green by propagation.

The present invention also includes methods of producing Rita Marie Green by asexual methods such as by cutting or by somatic cell culture.

The foregoing and other features and advantages of the invention will become more apparent from the following detailed description and accompanying photographs and figures.

BRIEF DESCRIPTION OF THE PHOTOGRAPHS

The file of this patent contains at least one drawing executed in color. Copies of this patent with color drawings will be provided by the Patent and Trademark Office upon request and payment of the necessary fee.

The following drawings are photographs of 'Rita Marie Green' taken in Azusa, Calif. between May and Jul. 1998.

DETAILED DESCRIPTION OF THE INVENTION

Figure 1:
FIG. 1 is an anterior view of the double flower bloom of Rita Marie Green showing the double flower structure made up of outer five-parted corolla limbs and inner five-parted petaloids.
Figure 2:
FIG. 2 is an posterior view of the double flower bloom of Rita Marie Green showing the outer five-parted corolla attached to the stem.
Figure 3:
FIG. 3 is a view of the foliage of Rita Marie Green showing elliptic evergreen leaves.

The present invention provides a Mandevilla plant (herein referred to as Double Mandevilla) having a double-flower consisting of an outer corolla of petals and an inner ring of petaloids (converted stamens). One embodiment of the present invention is the new and distinct variety of Mandevilla having double flowers called 'Rita Marie Green'.

Definitions

The following definitions are provided to better define the present invention. Terms not defined herein are to be understood according to their ordinary significance as employed by persons of ordinary skill in the relevant art.

The term "plant" or "variety" refers to whole plant specimens, sexually-reproduced progeny thereof, and any part of such a plant, including rootstock, budwood, hardwood or softwood cuttings, seeds, pollen, tissue culture cells, somatic embryos, or any other plant part that can be propagated (i.e., that is "propagable") by conventional methods.

"Sexual propagation" includes self-crossing and non-self-crossing of plants, for instance, self-crossing of Double Mandevilla (for example, any non-sterile Rita Marie Green) or crossing Double Mandevilla (for example, any non-sterile Rita Marie Green) with another Mandevilla variety that possess the essential characteristics of Double Mandevilla plants, in particular, double flowers.

The phrase "plant structure" as used herein refers to any part of a plant, including any tissue or organ, from a single cell to a complex multi-tissue organ such as a flower, root, shoot, leaf, stem, pollen cell, ovary, stamen, anther, carpel, pistil, bud, meristem, seed or cell culture.

The term "original stamens" means the number of stamens in the progenitor plant (the plant from which the Double Mandevilla was desired, not having double flowers). In the present invention, one or more of these original stamens and most preferably all of the original stamens have been converted to a petaloid.

The term "essentially derived" is used herein as defined in the International Convention for the Protection of New Varieties of Plants of Dec. 2, 1961, as revised on Mar. 19, 1991 (UPOV), according to which (Chap. V, Art. 14, par. (5)(b)) a variety is "essentially derived" from another variety ("the initial variety") when: (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and (iii) except for the differences which result from the act of derivation, it conforms to the initial variety in the expression of the essential characteristics that result from the genotype or combination of genotypes of the initial variety. Such essentially-derived varieties may be obtained for example by the selection of a natural or induced mutant, or of a somaclonal variant, the selection of a variant individual from plants of the initial variety, backcrossing, or transformation by genetic engineering (see UPOV, Chap. V, Art. 14, par. (5)(c)).

The 'Rita Marie Green', insofar as the applicant has been able to observe them, has consistently displayed the characteristics described herein. Double Mandevilla plants described herein also would be those that consistently have these double flowers.

Phenotypic Characteristics

The following is a detailed description of the invention based on plants grown at Haines City, Fla., and in Azusa, Calif. Color descriptions are according to the Royal Horticultural Society color charts. Other terminology is used herein in accordance with ordinary dictionary significance or as commonly used by those of ordinary skill in the relevant art, unless otherwise noted.

The parent plant of Rita Marie Green was found in a cultivated area (in a greenhouse) in Haines, City, Fla.

The Rita Marie Green has not been observed under all possible environmental conditions and its phenotype may vary significantly with variations in environment such as temperature, light intensity, and day length, without any variation in genotype. However, the essential characteristic, unique to the Double Mandevilla of the invention is double flowers, that is a Mandevilla flower having an outer corolla of petals and at least one and most preferably a plurality of petaloids within the outer corolla of petals. Most preferably, the double flowers have a generally concentric and complete (e.g. substantially encompassing three hundred sixty degrees) inner ring of petaloids.

In one embodiment, the inner petaloids are converted stamens. In one embodiment, all stamens may have been converted into petaloids, rendering the flower lacking in stamens and, therefore, sterile. It is also possible for some, but not all of the stamens to have been converted into petaloids such that the flower possesses an inner ring (which may be less than complete) of petaloids but also possess at least one stamen. In this case, the at least one stamen may be fertile so as to permit sexual reproduction of the plant.

One specific embodiment of the invention includes an inner ring of petaloids that are presented as being generally flattened and opened lying against the outer corolla, resembling the outer corolla, the petaloids having a length approximately equal to the petals of the outer corolla.

Another specific embodiment of the invention includes an inner ring of petaloids that are shorter than the petals of the outer corolla and that remain in a cluster forming a tight cluster habit of petaloids generally prohibiting a view of the inner throat and forming a "flower-within-flower" cluster. In one such embodiment, the petaloids may be fused or partially fused to form a tube or partial tube of petaloids. One embodiment of the invention includes a five-parted outer corolla and inner five-parted petaloids.

One embodiment of the invention includes Double Mandevilla plants having a double flower where the color of the corolla petals and the petaloids is primarily red to red-purple.

One specific embodiment of the invention is the variety 'Rita Marie Green '. This variety stabley produces several forms of double flowers, which thus display the double-flower characteristics of all Double Mandevilla flowers of the invention. In one form, the 'Rita Marie Green' plants have double flowers with outer five parted corolla limbs and inner five parted petaloids which overlay the corolla limbs, exposing the inner base of the tube. In a second form, the double flowers have outer five parted corolla limbs and inner five parted petaloids which are shorter than the corolla and remain in a cluster within outer corolla, forming a tight cluster habit of petaloids generally prohibiting a view of the inner throat and forming a "flower-within-flower" cluster. In rarer forms, the inner petaloids have been observed to have a folded almost rose-like appearance and alternatively a windmill-like appearance. In Rita Marie Green, these essential double-flower characteristics are present throughout successive generations. The petaloids are converted stamens and the plants of the invention observed to date thus exhibit no stamens and are, therefore, sterile. The essential characteristic of the Double Mandevilla plants of the invention is, therefore, double flowers.

Essential characteristics for all plants of the invention, would be established and transmitted through succeeding propagations.

Other characteristics exhibited by Double Mandevilla include the following (characteristics specifically exhibited by the Rita Marie Green are denoted by the phrase for Rita Marie Green):

FOLIAGE

Type: Evergreen.

Shape: Elliptic (linear to oblong).
  Apex: Long to short acuminate tip.
  Base: Cordate.

Length: about 9.5 cm to 15 cm.

Width: about 4.6 cm to 8.2 cm.

Color:
  Mature upperfoliage: Green, like RHS 139A to RHS 137A.
  Mature lower foliage: Green to yellow-green, like RHS 146B.
  Arrangement on stem: Opposite.
  Margins: Entire.

FLOWERS
  Arrangement: Axillary racemes.
  Structure: Double flower with outer corolla of petals and inner petaloids which is most preferably in the form of a complete ring of inner petaloids. Likely reproductive structures are sterile due to "double" flowers with typical five-numbered stamens converted to petaloids.
  Reproductive structures for 'Rita Marie Green':
    Style: Generally present, about 8 mm to 11 mm in length.
    Stamens: Absent, developed into showy petaloids.
  For 'Rita Marie Green' there are several double flower forms that have been observed, as follows:
  Form 1:
    Overall structure: Funnel-shaped. Outer five parted corolla limbs.
  Inner five parted petaloids. Petaloids overlay the corolla limbs exposing inner base of tube.
    Corolla:
      Color for 'Rita Marie Green':
        Corolla and petaloids: Red to red-purple, like RHS 58B and 58C.
        Petaloids (within throat): Slight striations of white, like RHS 155A and 155B, and yellow, like RHS 2 within 1 cm of base of inner throat.
        Corolla (within throat): Yellow, like RHS 2 within 2.5 cm of base of inner throat.
      Width: About 10.5 cm to 11.0 cm.
      Length of throat from calyx to corolla limb attachment: About 4.4 cm to 4.9 cm.
      Length of corolla from calyx to top of corolla: About 5.5 cm to 6.5 cm.
      Individual corolla limbs: 4.0 cm to 5.0 cm long, 3.5 cm to 5.5 cm wide. Asymmetrical in shape, ending in a short, abrupt tip.
    Petaloids (converted stamens):
      Individual petaloid length: About 4.0 cm to 4.5 cm.
      Individual petaloid width: About 3.5 cm to 5.0 cm.
      Petaloid attachment: About 1.5 cm above top of calyx.
      Petaloidfusion: Fused about 1.5 cm to 2.0 cm at base.
      Shape: Symmetrical short, abrupt tip. Petaloids are flattened and opened, resembling outer corolla. Length approximately equal to outer corolla, exhibiting a fully double appearance.
  Form 2:
    Overall structure: Funnel-shaped. Outer five parted corolla limbs. Inner five parted petaloids. Petaloids have defined difference, shorter than corolla and remaining in a cluster within outer corolla, not opening flat as in Form 1. Tight cluster habit of petaloids generally prohibits view of inner throat. Cluster of flower within flower.
    Corolla:
      Color:
        Corolla and petaloids: Red-purple group 62B, 62C and 62D, and red-purple group 58B and 58C.
        Petaloids (within throat): Exhibit white blotches and streaks of white group 155A and 155B, and yellow group 2 within 1 cm of base of inner throat.
        Corolla (within throat). Yellow group 2 within 1.5 cm of base of inner throat.
      Reproductive structure:
        Style. Generally present 8–11 cm in length.
        Stamens: Absent, developed into long petaloids.
      Width: About 9.0 cm to 10.5 cm.
      Length of throat from calyx to corolla limb attachment: About 4.3 cm to 4.8 cm.
      Length of corolla from calyx to top of corolla: About 6.0 cm to 7.0 cm.
      Individual corolla limbs: About 4.0 cm to 5.0 cm long, 3.6 cm to 4.6 cm wide. Asymmetrical in shape, ending in an abrupt tip.
    Petaloids (converted stamens):
      Individual petaloid length: About 3.5 cm to 5.0 cm.
      Individual petaloid width: About 4.0 cm to 5.2 cm.
      Petaloid attachment: About 1.5 cm above top of calyx.
      Petaloid fusion: Fused, sometimes separated about 2.0 cm at base.
      Shape: Somewhat symmetrical, undulate.
  Form 3. Rarely observed, inner five petaloids folded to provide a rose flower-like appearance.
    Overall Structure:
      Outer five parted corolla limbs, inner five parted petaloids.
      Width of corolla: 9–10.5 cm.
      Length of corolla throat from calyx to corolla limb attachment: 4.3–4.8 cm.
      Length of corolla from calyx to top of corolla: 6–7 cm.
      Outer corolla limbs: 4.5 cm. long.
      Inner petaloids: 4 cm long.
    Reproductive Structures:
      Style: Absent.
      Stamens: Absent.
    Shape: Inner petaloids flattened and opened, resembling outer corolla. Similar to Form #1.
    Color: Corolla and petaloids Red-purple group 58B and red-purple group 62B, 62C and 62D, with slight striations of white group 155A and 155B.
  Form 4: Rarely observed, inner five petaloids assume a windmill-like appearance.
    Overall structure: Outer five parted corolla limbs, inner five parted petaloids.
    Width of corolla: 9 cm.
    Length of corolla throat from calyx to corolla limb attachment: 4.5 cm.
    Length of corolla from calyx to top of corolla: 6 cm.
    Outer corolla limbs: 4 cm.
    Inner petaloids: 3 cm.
    Reproductive structures.
      Style. Absent
      Stamens: Absent
    Color:
      Corolla and petaloids: Red-purple group 58B and 58C and red-purple group 62A, 62B, 62C and 62D, interspersed with mottled white blotches on petaloids green-yellow at base 3 mm by 2 mm.

These additional characteristics are established in 'Rita Marie Green' and are transmitted through succeeding asexual propagations.

Asexual reproduction of 'Rita Marie Green' was performed by cuttings. Other conventional methods for propagation of Mandevilla varieties may also be used.

The above detailed description is in no way meant to narrow the scope of the invention which is to be interpreted in light of the claims. Having illustrated and described the principles of the present invention, it should be apparent to persons skilled in the art that the methods of the present invention can be modified in arrangement and detail without departing from such principles. Applicant claims all modifications that are within the spirit and scope of the appended claims.

What is claimed is:

1. A plant of a Mandevilla variety "Rita Marie Green" having at least one double flower.

2. The plant of claim 1 wherein said flowers have outer five parted corolla limbs and inner five parted petaloids, said petaloids overlaying the corolla limbs.

3. The plant of claim 1 wherein said flowers have outer five parted corolla limbs and inner five parted petaloids, said petaloids being shorter than the corolla and remaining in a cluster within outer corolla, forming a tight cluster habit of petaloids generally prohibiting a view of the inner throat.

4. A plant structure derived from the plant of claim 1.

5. A plant produced by propagating the Mandevilla variety 'Rita Marie Green' of claim 2.

6. A Mandevilla variety essentially derived from the plant of claim 1, wherein the essentially derived plant displays at least one double flower.

7. A plant part from the plant of claim 1.

8. Plant material from a plant of claim 1 which is capable of reproducing a double flowering Mandevilla plant.

9. A method of producing a double-flowering Mandevilla plant comprising propagating a double-flowering Mandevilla plant of the Rita Marie Green variety to produce a plurality of plants and selecting at least one double-flowering Mandevilla plant from said plurality of plants.

10. Asexually produced progeny of the double-flowering Mandevilla plant according to claim 1.

* * * * *